United States Patent
Yang et al.

(10) Patent No.: US 12,415,979 B2
(45) Date of Patent: Sep. 16, 2025

(54) MEMBRANE BIOREACTOR FOR DEEP-SEA COLD SEEPS AND ONLINE ENVIRONMENTAL PARAMETER MEASUREMENT SYSTEM

(71) Applicants: GUANGDONG LABORATORY OF SOUTHERN OCEAN SCIENCE AND ENGINEERING (GUANGZHOU), Guangdong (CN); GUANGDONG UNIVERSITY OF TECHNOLOGY, Guangdong (CN)

(72) Inventors: Zhifeng Yang, Guangdong (CN); Jingchun Feng, Guangdong (CN); Si Zhang, Guangdong (CN); Yi Wang, Guangdong (CN); Song Zhong, Guangdong (CN); Yanpeng Cai, Guangdong (CN)

(73) Assignees: GUANGDONG LABORATORY OF SOUTHERN OCEAN SCIENCE AND ENGINEERING (GUANGZHOU), Guangdong (CN); GUANGDONG UNIVERSITY OF TECHNOLOGY, Guangdong (CN)

( * ) Notice: Subject to any disclaimer, the term of this patent is extended or adjusted under 35 U.S.C. 154(b) by 0 days.

(21) Appl. No.: 18/019,826

(22) PCT Filed: Mar. 30, 2022

(86) PCT No.: PCT/CN2022/084122
§ 371 (c)(1),
(2) Date: Feb. 6, 2023

(87) PCT Pub. No.: WO2023/173496
PCT Pub. Date: Sep. 21, 2023

(65) Prior Publication Data
US 2024/0254420 A1   Aug. 1, 2024

(30) Foreign Application Priority Data

Mar. 15, 2022   (CN) .......................... 202210251231.4

(51) Int. Cl.
*C12M 1/12* (2006.01)
*C12M 1/00* (2006.01)
*C12M 1/34* (2006.01)

(52) U.S. Cl.
CPC ............ *C12M 25/04* (2013.01); *C12M 23/22* (2013.01); *C12M 29/14* (2013.01); *C12M 29/24* (2013.01);
(Continued)

(58) Field of Classification Search
CPC ...... C12M 25/04; C12M 23/22; C12M 29/14; C12M 29/24; C12M 41/12; C12M 41/34; C12M 41/40
(Continued)

(56) References Cited

U.S. PATENT DOCUMENTS

2019/0309256 A1   10/2019   Norddahl et al.

FOREIGN PATENT DOCUMENTS

| CN | 103540522 | 1/2014 |
| CN | 106336004 | 1/2017 |

(Continued)

OTHER PUBLICATIONS

CN111894529A Machine English Translation (Year: 2020).*
(Continued)

*Primary Examiner* — Michael L Hobbs
*Assistant Examiner* — Lenora A Abel
(74) *Attorney, Agent, or Firm* — JCIPRNET

(57) ABSTRACT

The present invention provides a membrane bioreactor for deep-sea cold seeps. The bioreactor is used for simulating a biomembrane growth process during anaerobic oxidation of
(Continued)

methane (AOM) in the cold seeps and monitoring changes of environmental conditions thereof. The present invention further provides an online environmental parameter measurement system for a membrane biological reaction in the deep-sea cold seeps. The system includes a fluid supply unit used for generating saturated methane fluid and injecting the saturated methane fluid into the membrane bioreactor for the deep-sea cold seeps at a microflow, and a pressurization system used for ensuring stability and consistency of internal environmental pressure of the system in a simulation process.

12 Claims, 3 Drawing Sheets

(52) U.S. Cl.
CPC ............ *C12M 41/12* (2013.01); *C12M 41/34* (2013.01); *C12M 41/40* (2013.01)
(58) Field of Classification Search
USPC ..................................................... 435/297.5
See application file for complete search history.

(56) References Cited

FOREIGN PATENT DOCUMENTS

| CN | 209024535 | 6/2019 | | |
|---|---|---|---|---|
| CN | 110591893 | 12/2019 | | |
| CN | 111551671 | 8/2020 | | |
| CN | 111894529 | 11/2020 | | |
| CN | 111894529 A | * 11/2020 | ............ | E21B 43/01 |
| CN | 112964833 | 6/2021 | | |
| CN | 113051710 | 6/2021 | | |

OTHER PUBLICATIONS

Dai; Jinping et al., "The application of molecular biology technology in the diversity study of methane—producing archaea", Heilongjiang Animal Science and Veterinary Medicine, Feb. 2016, with English abstract, pp. 43-46, No. 2.

Shimshon Belkin et al., "Ocean and Health: Pathogens in the Marine Environment", Jul. 2015, with partial English translation thereof, pp. 1-8.

Fengping Wang et al., "Biodiversity of deep-sea microorganisms", Biodiversity Science, Jul. 2013, with English abstract, pp. 445-455, vol. 21, No. 4.

Li; Jiang et al., "Advances in Research on Anaerobic Methanotrophs", Chin J Appl Environ Biol, Oct. 25, 2011, with English abstract, pp. 763-766, vol. 17, No. 5.

"International Search Report (Form PCT/ISA/210) of PCT/CN2022/084122," mailed on Sep. 27, 2022, pp. 1-5.

* cited by examiner

MEMBRANE BIOREACTOR FOR DEEP-SEA COLD SEEPS AND ONLINE ENVIRONMENTAL PARAMETER MEASUREMENT SYSTEM

CROSS-REFERENCE TO RELATED APPLICATION

This application is a 371 of international application of PCT application serial no. PCT/CN2022/084122, filed on Mar. 30, 2022, which claims the priority benefit of China application no. 202210251231.4, filed on Mar. 15, 2022. The entirety of each of the above mentioned patent applications is hereby incorporated by reference herein and made a part of this specification.

TECHNICAL FIELD

The present invention relates to the technical field of marine environmental ecological engineering, in particular to a membrane bioreactor for deep-sea cold seeps and an online environmental parameter measurement system.

BACKGROUND

Since the discovery of cold seeps on the seafloor nearly half a century ago, the resource and environmental benefits of cold seeps have been widely recognized around the world. Cold seeps are fluid activities in which gases such as methane, hydrogen sulfide, and carbon dioxide under the seafloor leak out of the seafloor and enter seawater, driven by geological structures or pressure changes. The temperature around cold seeps is typically 3-5° C., and cold seeps are found mainly in subduction zones and on passive continental margins rich in organic matter. Cold seeps transport dissolved and gaseous compounds upward, maintaining important chemosynthetic ecosystems in the deep sea. Anaerobic oxidation of methane (AOM) by archaea is the most important reaction, providing an important source of material for sulfur-related biogeochemistry and carbonate mineral precipitation in the cold seeps, as well as an important source of carbon and energy for the growth of metazoa in the dark world. The AOM-dependent cold seep ecosystem is an important window into the Earth's deep biosphere and an important landmark in the search for gas hydrates.

At present, due to the limitations of observation and fidelity study, the mechanism of AOM in cold seeps is not fully understood, the role of AOM augmentation and restricted environmental conditions is not perfect, and especially the characteristics and microscopic mechanism of biomembrane formation of deep-sea archaea under the action of AOM is not clear. There is an urgent need for long-period simulation of a deep-sea cold seep system, online measurement of a biomembrane growth process during the action of AOM, and monitoring on changes of environmental parameters thereof.

A device for deep-sea cold seep biological high-pressure temperature-controlled simulation culture is disclosed in the prior art, and includes a mixing chamber, a high-pressure chamber, a high-pressure filter device and a variety of valves, which are connected through high-pressure pipelines. In the high-pressure chamber, a deep-sea high temperature or low temperature high hydrostatic pressure environment is realized through a high-pressure pump and a temperature control system, and an enrichment filter device and a fixing device are provided at the same time. Although the device solves the technical problems about culture, enrichment and fixation of large organisms and microbial bacteria under high pressure, the device is not applicable to simulating the AOM process and cannot simulate and monitor the growth process and environment of a biomembrane during the action of AOM.

SUMMARY

In order to overcome at least one of the above-mentioned technical defects, the present invention provides a membrane bioreactor for deep-sea cold seeps and an online environmental parameter measurement system, which realize the study of biomembrane growth characteristics of a process of anaerobic oxidation of methane (AOM) in the cold seeps and the influence of environmental conditions thereof, and provide an important basis for correct understanding of anaerobic oxidation of methane in a deep sea and measurement of environmental parameters.

In order to solve the above-mentioned technical problems, the present invention adopts the following technical solutions.

A membrane bioreactor for deep-sea cold seeps includes a control and acquisition terminal, a sediment simulation chamber, a seawater simulation chamber, a sensor group, a pressure-resistant membrane biological assembly, an online pressure-holding biomembrane sampling element, a resistivity measurement system, a pressure regulation assembly and an ultrasonic observation assembly; the sediment simulation chamber is disposed below the seawater simulation chamber, and is in flanged connection to the seawater simulation chamber; the sensor group is disposed in the sediment simulation chamber and the seawater simulation chamber, and a signal output end of the sensor group is electrically connected to the control and acquisition terminal; the pressure-resistant membrane biological assembly is disposed in the seawater simulation chamber for monitoring formation of a methanotroph and sulfate reducing bacteria biomembrane in a seawater environment; the online pressure-holding biomembrane sampling element is disposed on a top of the seawater simulation chamber, and a control end of the online pressure-holding biomembrane sampling element is electrically connected to the control and acquisition terminal for scraping biomembrane samples from different positions of the pressure-resistant membrane biological assembly for sequencing analysis in a formation process of the biomembrane; the resistivity measurement system is disposed in the sediment simulation chamber, and a signal output end of the resistivity measurement system is electrically connected to the control and acquisition terminal for monitoring and measuring saturation changes of methane hydrate formation in sediments in a process of methane seepage simulation; the pressure regulation assembly is connected to the seawater simulation chamber through a pipeline, and a control end of the pressure regulation assembly is electrically connected to the control and acquisition terminal for regulating and controlling pressure in the reactor to ensure pressure stability in the reactor; and an ultrasonic probe of the ultrasonic observation assembly is disposed in the seawater simulation chamber for monitoring thickness changes of the biomembrane on the pressure-resistant membrane biological assembly and outputting a signal to the control and acquisition terminal.

In the above-mentioned solution, the membrane bioreactor for the deep-sea cold seeps is of a corrosion and pressure resistant structure, a membrane biological assembly in a high-pressure environment is constructed through the pressure-resistant membrane biological assembly for membrane forming and growth of microorganisms in the deep-sea cold seeps, in addition, the thickness changes of the biomembrane on the membrane assembly are measured online through monitoring of the ultrasonic observation assembly, and the biomembrane samples are obtained by pressure holding under a high-pressure condition for sequencing analysis, such that online monitoring of the biomembrane during action of AOM is realized, the research on the biomembrane growth characteristics of the process of anaerobic oxidation of methane in the cold seeps and the influence of environmental conditions thereof is realized, and an important basis is provided for the correct understanding of anaerobic oxidation of methane in the deep sea and the measurement of environmental parameters.

The sensor group includes temperature sensors, a methane sensor and a pressure sensor; the temperature sensors are disposed in the sediment simulation chamber and the seawater simulation chamber for monitoring changes of an environmental temperature in the sediment simulation chamber and the seawater simulation chamber, and signal output ends of the temperature sensors are electrically connected to the control and acquisition terminal; the methane sensor is disposed in the seawater simulation chamber for monitoring changes of methane concentration in the seawater simulation chamber, and a signal output end of the methane sensor is electrically connected to the control and acquisition terminal; and the pressure sensor is disposed in the seawater simulation chamber for monitoring changes of pressure in the reactor, and a signal output end of the pressure sensor is electrically connected to the control and acquisition terminal.

The pressure-resistant membrane biological assembly is a porous membrane assembly sintered from seawater corrosion-resistant and pressure-resistant titanium alloy powder, and is suspended in the seawater simulation chamber.

The online pressure-holding biomembrane sampling element includes a telescopic pressure-resistant cylinder, a sampling ring device and a pressure-holding device; the telescopic pressure-resistant cylinder is disposed on the top of the seawater simulation chamber; the sampling ring device is placed in the telescopic pressure-resistant cylinder; the pressure-holding device is fixedly connected outside the telescopic pressure-resistant cylinder in a sleeving manner; and a control end of the sampling ring device and a control end of the pressure-holding device are both electrically connected to the control and acquisition terminal.

In the above-mentioned solution, the sampling ring device is placed in the telescopic pressure-resistant cylinder for scraping the biomembrane samples from different positions of the pressure-resistant membrane biological assembly for sequencing analysis in the formation process of the biomembrane. When the biomembrane requires to be scraped, considering a pressure difference inside and outside the reactor, the pressure-holding device is controlled to be turned off first, inert gas is injected automatically for pressure consistency with the inside of the reactor, then an internal valve of the pressure-holding device is opened, the sampling ring device is controlled to scrape biomembrane samples from different positions of the pressure-resistant membrane biological assembly and draws away from the internal valve of the pressure-holding device, finally, the internal valve of the pressure-holding device is closed, an external valve of the pressure-holding device is opened, and the whole operation of scraping the biomembrane is completed.

The pressure regulation assembly includes a PID valve and a gas-liquid storage tank; the gas-liquid storage tank is connected to the seawater simulation chamber through a pipeline; and the PID valve is disposed on the pipeline and electrically connected to the control and acquisition terminal.

In the above-mentioned solution, in the whole process of simulation or application of the reactor, the PID valve may effectively ensure the pressure stability in the reactor through PID control. At the same time, the gas-liquid storage tank with a temperature and pressure monitoring function is used for collecting and measuring the volume of gas and liquid discharged from the reactor.

The ultrasonic observation assembly further includes an acoustic wave generator-oscilloscope; and a signal output end of the ultrasonic probe is electrically connected to a signal input end of the acoustic wave generator-oscilloscope and the control and acquisition terminal for monitoring the thickness changes of the biomembrane on the pressure-resistant membrane biological assembly.

The membrane bioreactor for the deep-sea cold seeps further includes pressure-resistant visible windows provided in the seawater simulation chamber, and double valve piston samplers disposed in the sediment simulation chamber and the seawater simulation chamber.

In the above-mentioned solution, the pressure-resistant visible windows are provided to facilitate observation of formation of the biomembrane, and the pressure-resistant visible windows are disposed in a front side and a rear side of the seawater simulation chamber respectively, such that the formation process of the biomembrane can be shot and observed through the pressure-resistant visible windows. The double valve piston samplers are disposed in different layers of the sediment simulation chamber and the seawater simulation chamber for sampling and analyzing changes in chemical composition and concentration of samples, as well as changes in biomembrane thickness and microbial groups.

The membrane bioreactor for the deep-sea cold seeps further includes a water bath jacket disposed around the reactor, and a control end of the water bath jacket is electrically connected to the control and acquisition terminal.

In the above-mentioned solution, in order to facilitate window observation, the reactor adopts the water bath jacket for a jacketed water bath, the water bath jacket is disposed around the reactor, and is filled with a circulating refrigeration liquid, and an insulation layer is disposed on an outer wall of the water bath jacket to ensure a low-temperature environment of the sediment simulation chamber and the seawater simulation chamber.

In the above-mentioned solution, the control and acquisition terminal is used for realizing monitoring of changes of various environmental data in the process of methane seepage simulation, as well as real-time acquisition, processing, storage, image output and other functions.

In the above solution, during application simulation, an inlet and an outlet of the reactor are opened at the same time to maintain a continuous seepage process, which may simulate a seafloor environment close to the real environment, and under this condition, the situation of material exchange between an environmental medium of methane seepage and the ambience is studied.

This solution further provides an online environmental parameter measurement system for a membrane biological reaction in deep-sea cold seeps. The system includes the above-mentioned membrane bioreactor for the deep-sea cold seeps, a fluid supply unit and a pressurization system; the fluid supply unit is configured to generate saturated methane fluid and inject the saturated methane fluid into the membrane bioreactor for the deep-sea cold seeps at a microflow; the membrane bioreactor for the deep-sea cold seeps simulates a biomembrane growth process during anaerobic oxidation of methane in the cold seeps and monitors changes of environmental conditions thereof; the membrane bioreactor for the deep-sea cold seeps and the fluid supply unit are both connected to the pressurization system to ensure stability and consistency of internal environmental pressure of the system in a simulation process; and the fluid supply unit and the pressurization system are both electrically connected to a control and acquisition terminal to realize information interaction.

The fluid supply unit includes a pressure-resistant methane dissolution vessel, an injection pump, a low-temperature water bath vessel, a mechanical stirring device, a back pressure valve, a microflow pump and a seawater culture medium preparation vessel; the methane dissolution vessel is disposed in the low-temperature water bath vessel to ensure that methane-containing fluid is unable to cause heat flow disturbance due to a temperature difference when entering the membrane bioreactor for the deep-sea cold seeps, and the simulation process is not affected; the methane dissolution vessel is provided with a gas inlet, a liquid inlet and a liquid outlet; the methane dissolution vessel is connected to the pressurization system through the gas inlet; the methane dissolution vessel is connected to the seawater culture medium preparation vessel and the injection pump in sequence through the liquid inlet; the methane dissolution vessel is connected to the microflow pump through the liquid outlet, and the saturated methane fluid is injected into the membrane bioreactor for the deep-sea cold seeps through the microflow pump at a microflow; a second temperature sensor and a second pressure sensor are disposed in the methane dissolution vessel for monitoring temperature and pressure data in the methane dissolution vessel and transmitting the data to the control and acquisition terminal; the mechanical stirring device is disposed on a top of the methane dissolution vessel for enhancing solute dissolution in the methane dissolution vessel; and the back pressure valve is disposed on the top of the methane dissolution vessel for ensuring that the methane dissolution vessel completes a dissolution process at set pressure.

In the above-mentioned solution, the methane dissolution vessel is disposed in the low-temperature water bath vessel further for making the system in line with the characteristic of a small temperature difference with an ambient medium when the methane-containing fluid seeps into a seepage area under a seafloor condition closer to the real condition.

In a simulation process of the fluid supply unit, a temperature of the methane dissolution vessel is set to be consistent with that of the membrane bioreactor for the deep-sea cold seeps, and is an actual seafloor temperature, but pressure of the methane dissolution vessel needs to be monitored to be lower than phase equilibrium pressure of methane hydrate formation under the temperature condition, so as to avoid formation of methane hydrate in the methane dissolution vessel.

The pressurization system includes an air compressor, a booster pump, a gas storage tank, a regulating valve and a pipe valve member; the pressurization system is connected to the gas inlet of the fluid supply unit and a gas inlet of the membrane bioreactor for the deep-sea cold seeps through the pipe valve member; the air compressor is connected to an input end of the gas storage tank through the booster pump; and an output end of the gas storage tank is provided with the regulating valve, and connected to the pipe valve member through the regulating valve for injecting gas with set components into the fluid supply unit and the membrane bioreactor for the deep-sea cold seeps at a set flow.

The above-mentioned solution is implemented with the capacity of simulating the continuous methane seepage process under the deep-sea in-situ temperature and pressure environment conditions. By constructing the membrane biological assembly in the high-pressure environment for membrane forming and growth of the microorganisms in the deep-sea cold seeps, measuring the thickness changes of the biomembrane on the membrane assembly online through ultrasonic monitoring, and obtaining the biomembrane samples by pressure holding under the high-pressure condition for sequencing analysis, the characteristics of anaerobic oxidation of methane in the cold seeps and the influence of environmental conditions on anaerobic oxidation of methane are quantitatively studied. Compared with existing simulations of methane biochemical conversion processes in deep-sea cold seeps, which ignore the characteristics of methane dissolution and phase transformation in a high-pressure and low-temperature environment, this solution simultaneously monitors the amount of methane dissolution and phase transformation in the reactor during methane seepage, thereby more accurately quantitatively studying the characteristics of anaerobic oxidation of methane in the cold seeps. An important technical tool is provided for accurately understanding the biochemical conversion process and mechanism of methane release from the deep-sea floor.

Compared with the prior art, the technical solution of the present invention has the following beneficial effects.

The present invention provides the membrane bioreactor for the deep-sea cold seeps and the online environmental parameter measurement system. In order to quantitatively study the efficiency of AOM in utilizing the deep-sea methane seepage, the content of methane dissolved after entering the cold seeps and the content of natural gas hydrate generated by phase change are monitored, and the methane content used for AOM is measured more accurately. By constructing the membrane biological assembly in the reactor, performing online monitoring on the biomembrane during action of AOM, and performing pressure-holding sampling and sequencing analysis, the biomembrane growth characteristics of a process of anaerobic oxidation of methane in the cold seeps and the influence of environmental conditions thereof are studied, providing an important research and test method for correct understanding of anaerobic oxidation of methane in the deep sea and measurement of environmental parameters.

1 denotes a sediment simulation chamber; 2 denotes a seawater simulation chamber; 21 denotes a pressure-resistant visible window; 3 denotes a sensor group; 31 denotes a temperature sensor; 32 denotes a methane sensor; 33 denotes a pressure sensor; 4 denotes a pressure-resistant membrane biological assembly; 5 denotes an online pressure-holding biomembrane sampling element; 6 denotes a resistivity measurement system; 7 denotes a pressure regulation assembly; 71 denotes a PID valve; 72 denotes a gas-liquid storage tank; 8 denotes an ultrasonic observation assembly; 81 denotes an ultrasonic probe; 82 denotes an acoustic wave generator-oscilloscope; 9 denotes a control and acquisition terminal; 10 denotes a water bath jacket; 11 denotes a double valve piston sampler; 101 denotes a membrane bioreactor for deep-sea cold seeps; 102 denotes a fluid supply unit; 1021 denotes a methane dissolution vessel; 10211 denotes a second temperature sensor; 10212 denotes a second pressure sensor; 1022 denotes an injection pump; 1023 denotes a low-temperature water bath vessel; 1024 denotes a mechanical stirring device; 1025 denotes a back pressure valve; 1026 denotes a microflow pump; 1027 denotes a seawater culture medium preparation vessel; and 103 denotes a pressurization system.

DETAILED DESCRIPTION

The accompanying drawings are for illustrative purposes merely and should not be construed as limitations on this patent.

The following examples are complete use examples with rich contents.

In order to better illustrate the examples, some parts in the accompanying drawings are omitted, enlarged, or reduced, and do not represent the size of actual products.

It may be understood by those skilled in the art that some well-known structures and descriptions thereof may be omitted from the accompanying drawings.

The technical solutions of the present invention are further described below in conjunction with the accompanying drawings and examples.

Example 1

Figure 1:
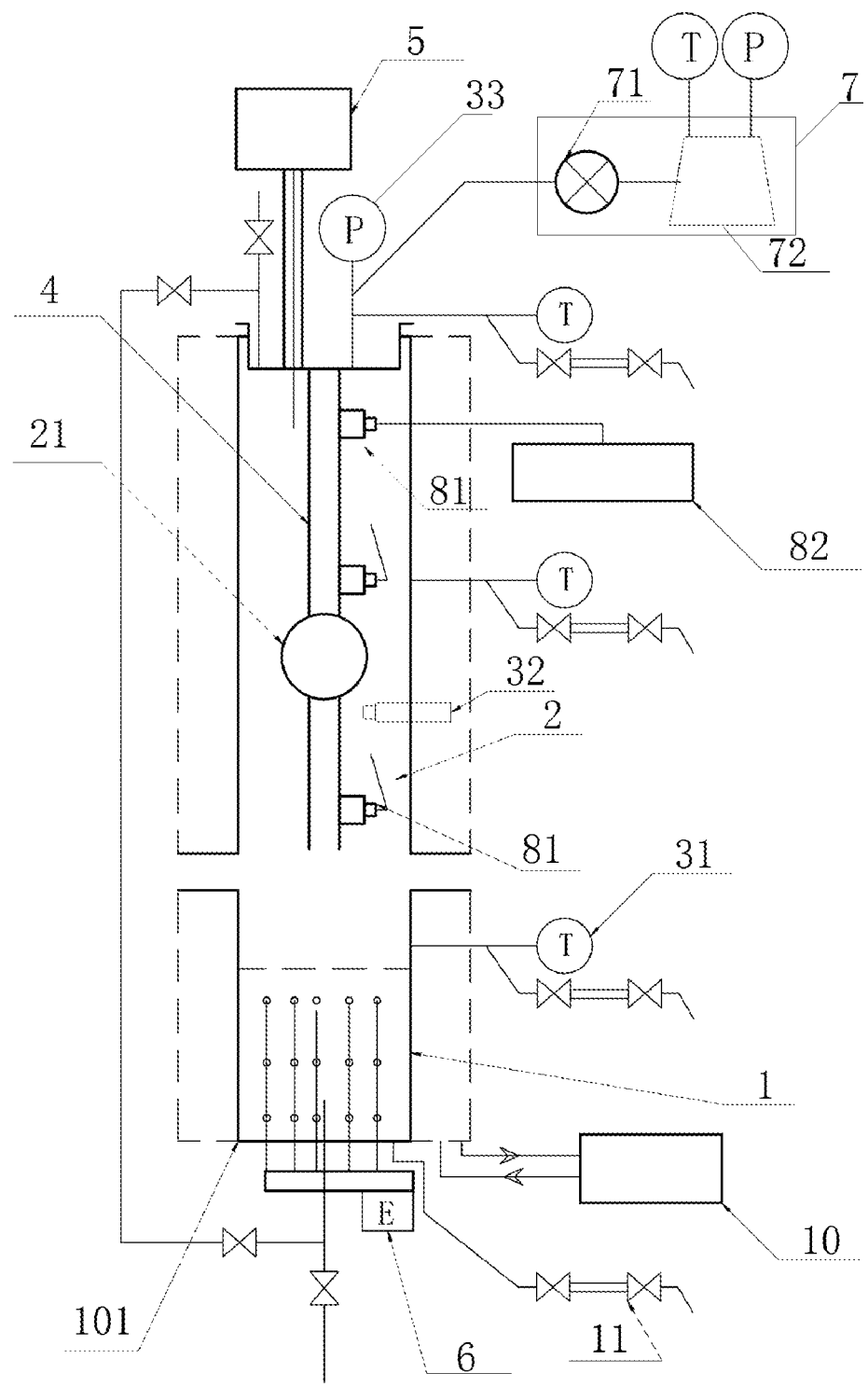
FIG. 1 is a schematic structural diagram of a membrane bioreactor for deep-sea cold seeps according to the present invention.
Figure 3:
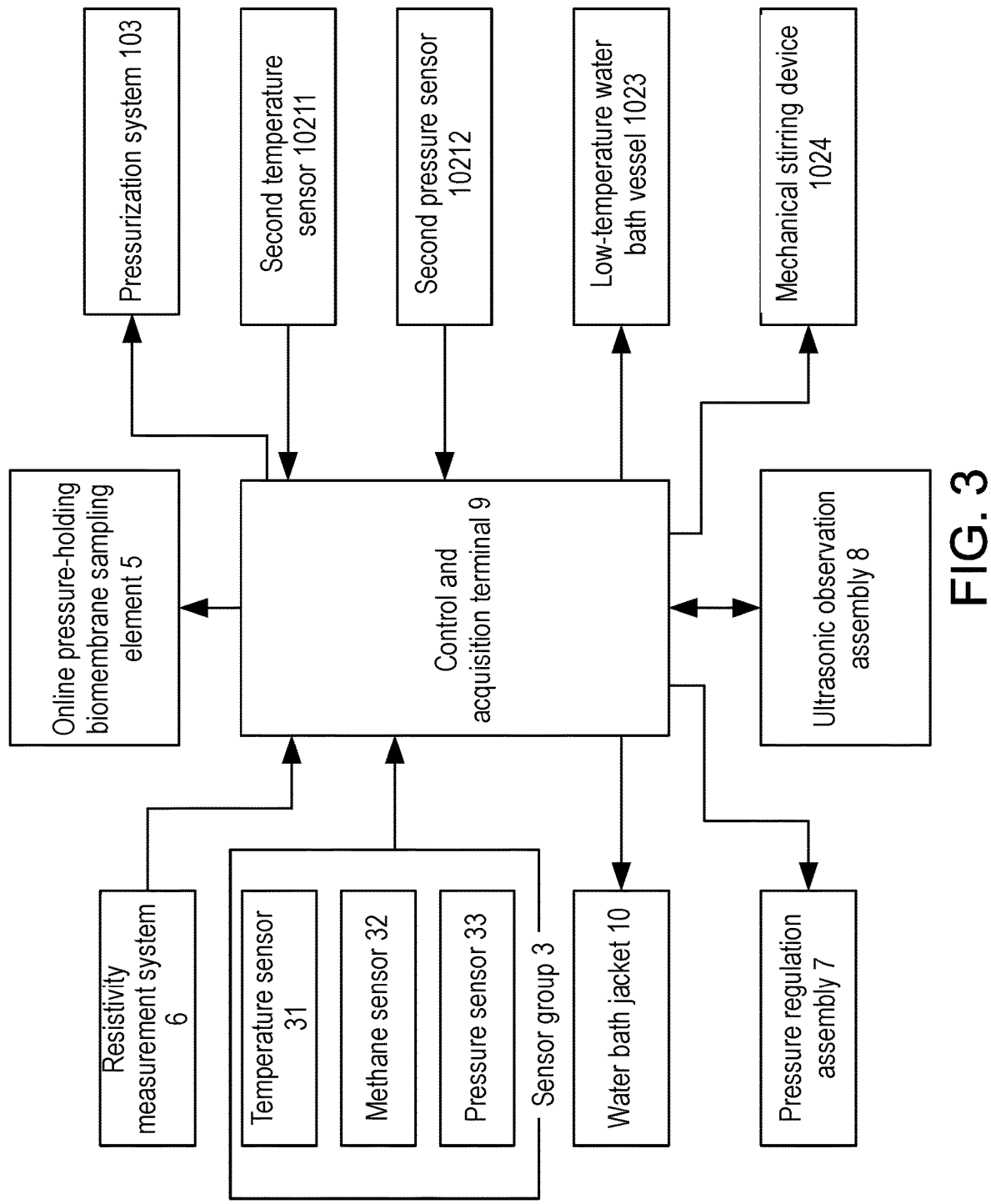
FIG. 3 is a schematic diagram of electrical connection of a control and acquisition terminal of an online environmental parameter measurement system according to the present invention.

As shown in FIG. 1 and FIG. 3, a membrane bioreactor for deep-sea cold seeps includes a control and acquisition terminal 9, a sediment simulation chamber 1, a seawater simulation chamber 2, a sensor group 3, a pressure-resistant membrane biological assembly 4, an online pressure-holding biomembrane sampling element 5, a resistivity measurement system 6, a pressure regulation assembly 7 and an ultrasonic observation assembly 8. The sediment simulation chamber 1 is disposed below the seawater simulation chamber 2, and is in flanged connection to the seawater simulation chamber 2. The sensor group 3 is disposed in the sediment simulation chamber 1 and the seawater simulation chamber 2 respectively, and a signal output end of the sensor group 3 is electrically connected to the control and acquisition terminal 9. The pressure-resistant membrane biological assembly 4 is disposed in the seawater simulation chamber 2 for monitoring formation of a colony biomembrane in a seawater environment. The online pressure-holding biomembrane sampling element 5 is disposed on a top of the seawater simulation chamber 2, and a control end of the online pressure-holding biomembrane sampling element is electrically connected to the control and acquisition terminal 9 for scraping biomembrane samples from different positions of the pressure-resistant membrane biological assembly 4 for sequencing analysis in a formation process of the biomembrane. The resistivity measurement system 6 is disposed in the sediment simulation chamber 1, and a signal output end of the resistivity measurement system is electrically connected to the control and acquisition terminal 9 for monitoring and measuring saturation changes of methane hydrate formation in sediment in a process of methane seepage simulation. The pressure regulation assembly 7 is connected to the seawater simulation chamber 2 through a pipeline, and a control end of the pressure regulation assembly is electrically connected to the control and acquisition terminal 9 for regulating and controlling pressure in the reactor to ensure pressure stability in the reactor. An ultrasonic probe 81 of the ultrasonic observation assembly 8 is disposed in the seawater simulation chamber 2 for monitoring thickness changes of the biomembrane on the pressure-resistant membrane biological assembly 4 and outputting a signal to the control and acquisition terminal 9.

More specifically, the sensor group 3 includes temperature sensors 31, a methane sensor 32 and a pressure sensor 33. The temperature sensors 31 are disposed in the sediment simulation chamber 1 and the seawater simulation chamber 2 for monitoring changes of an environmental temperature in the sediment simulation chamber 1 and the seawater simulation chamber 2, and signal output ends of the temperature sensors are electrically connected to the control and acquisition terminal 9. The methane sensor 32 is disposed in the seawater simulation chamber 2 for monitoring changes of methane concentration in the seawater simulation chamber 2, and a signal output end of the methane sensor is electrically connected to the control and acquisition terminal 9. The pressure sensor 33 is disposed in the seawater simulation chamber 2 for monitoring changes of pressure in the reactor, and a signal output end of the pressure sensor is electrically connected to the control and acquisition terminal 9.

More specifically, the pressure-resistant membrane biological assembly 4 is a porous membrane assembly sintered from seawater corrosion-resistant and pressure-resistant titanium alloy powder, and is suspended in the seawater simulation chamber 2.

More specifically, the online pressure-holding biomembrane sampling element 5 includes a telescopic pressure-resistant cylinder, a sampling ring device and a pressure-holding device. The telescopic pressure-resistant cylinder is disposed on the top of the seawater simulation chamber 2. The sampling ring device is placed in the telescopic pressure-resistant cylinder. The pressure-holding device is fixedly connected outside the telescopic pressure-resistant cylinder in a sleeving manner. A control end of the sampling ring device and a control end of the pressure-holding device are both electrically connected to the control and acquisition terminal 9.

In a specific implementation process, the sampling ring device is placed in the telescopic pressure-resistant cylinder for scraping the biomembrane samples from different positions of the pressure-resistant membrane biological assembly 4 for sequencing analysis in the formation process of the biomembrane. When the biomembrane requires to be scraped, considering a pressure difference inside and outside the reactor, the pressure-holding device is controlled to be turned off first, inert gas is injected automatically for pressure consistency with the inside of the reactor, then an internal valve of the pressure-holding device is turned on, the sampling ring device is controlled to scrape biomembrane samples from different positions of the pressure-resistant membrane biological assembly 4 and draws away from the internal valve of the pressure-holding device, finally, the internal valve of the pressure-holding device is closed, an external valve of the pressure-holding device is opened, and the whole operation of scraping the biomembrane is completed.

More specifically, the pressure regulation assembly 7 includes a PID valve 71 and a gas-liquid storage tank 72. The gas-liquid storage tank 72 is connected to the seawater simulation chamber 2 through a pipeline. The PID valve 71 is disposed on the pipeline and electrically connected to the control and acquisition terminal 9.

In the whole process of simulation or application of the reactor, the PID valve 71 may effectively ensure the pressure stability in the reactor through PID control. At the same time, the gas-liquid storage tank 72 with a temperature and pressure monitoring function is used for collecting and measuring the volume of gas and liquid discharged from the reactor.

More specifically, the ultrasonic observation assembly 8 further includes an acoustic wave generator-oscilloscope 82. A signal output end of the ultrasonic probe 81 is electrically connected to a signal input end of the acoustic wave generator-oscilloscope 82 and the control and acquisition terminal 9.

More specifically, the membrane bioreactor 101 for the deep-sea cold seeps further includes pressure-resistant visible windows 21 provided in the seawater simulation chamber 2, and double valve piston samplers 11 disposed in the sediment simulation chamber 1 and the seawater simulation chamber 2.

In a specific implementation process, the pressure-resistant visible windows 21 are provided to facilitate observation of formation of the biomembrane, and the pressure-resistant visible windows are disposed in a front side and a rear side of the seawater simulation chamber respectively, such that the formation process of the biomembrane can be shot and observed through the pressure-resistant visible windows 21. The double valve piston samplers 11 are disposed in different layers of the sediment simulation chamber 1 and the seawater simulation chamber 2 for sampling and analyzing changes in chemical composition and concentration of samples, as well as changes in biomembrane thickness and microbial groups.

More specifically, the membrane bioreactor 101 for the deep-sea cold seeps further includes a water bath jacket 10 disposed around the reactor, and a control end of the water bath jacket is electrically connected to the control and acquisition terminal 9.

In a specific implementation process, in order to facilitate window observation, the reactor adopts the water bath jacket 10 for a jacketed water bath, the water bath jacket 10 is disposed around the reactor, and is filled with a circulating refrigeration liquid, and an insulation layer is disposed on an outer wall of the water bath jacket 10 to ensure a low-temperature environment of the sediment simulation chamber 1 and the seawater simulation chamber 2.

In a specific implementation process, the control and acquisition terminal 9 is used for realizing monitoring of changes in various environmental data in the process of methane seepage simulation, as well as real-time acquisition, processing, storage, image output and other functions.

In a specific implementation process, during application simulation, an inlet and an outlet of the reactor are opened at the same time to maintain a continuous seepage process, which may simulate a seafloor environment close to the real environment, and under this condition, the situation of material exchange between an environmental medium of methane seepage and the ambience is studied. The membrane bioreactor 101 for the deep-sea cold seeps is of a corrosion and pressure resistant structure, a membrane biological assembly in a high-pressure environment is constructed through the pressure-resistant membrane biological assembly 4 for membrane forming and growth of microorganisms in the deep-sea cold seeps, in addition, the thickness changes of the biomembrane on the membrane assembly are measured online through monitoring of the ultrasonic observation assembly, and the biomembrane samples are obtained by pressure holding under a high-pressure condition for sequencing analysis, such that online monitoring of the biomembrane during action of AOM is realized, the research on the biomembrane growth characteristics of anaerobic oxidation of methane (AOM) in the cold seeps and the influence of environmental conditions thereon is realized, and an important basis is provided for correct understanding of anaerobic oxidation of methane in the deep sea and measurement of environmental parameters.

Example 2

Figure 2:
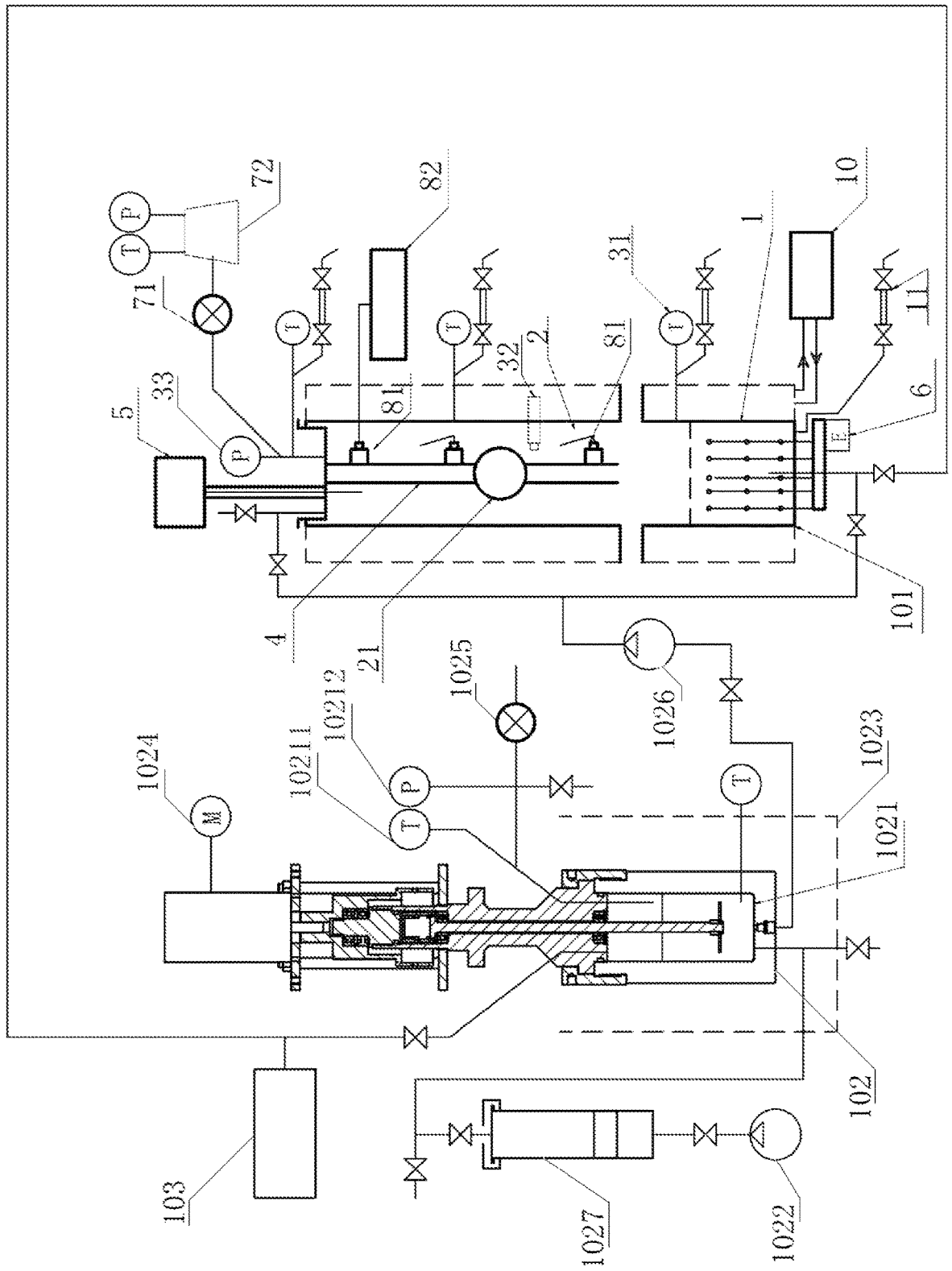
FIG. 2 is a schematic structural diagram of an online environmental parameter measurement system according to the present invention.

More specifically, on the basis of Example 1, as shown in FIG. 2 and FIG. 3, an online environmental parameter measurement system for a membrane biological reaction in deep-sea cold seeps is provided. The system includes the membrane bioreactor 101 for the deep-sea cold seeps, a fluid supply unit 102 and a pressurization system 103. The fluid supply unit 102 is configured to generate saturated methane fluid and inject the saturated methane fluid into the membrane bioreactor 101 for the deep-sea cold seeps at a microflow. The membrane bioreactor 101 for the deep-sea cold seeps simulates a biomembrane growth process during anaerobic oxidation of methane in the cold seeps and monitors changes of environmental conditions thereof. The membrane bioreactor 101 for the deep-sea cold seeps and the fluid supply unit 102 are both connected to the pressurization system 103 to ensure stability and consistency of internal environmental pressure of the system in a simulation process. The fluid supply unit 102 and the pressurization system 103 are both electrically connected to a control and acquisition terminal 9 to realize information interaction.

In a specific implementation process, this example may simulate the methane seepage process continuously under deep-sea in-situ temperature and pressure conditions in an open system mode. Open system simulation is helpful to discharge of metabolic waste during microbial mediated anaerobic oxidation of methane, and is helpful to improving efficiency of methane biochemical conversion and microbial activity, and boundary conditions are closer to the methane seepage process in a real seafloor environment. At the same time, this example can quantitatively monitor and analyze the thickness, distribution and microbial groups of a biomembrane formed by microorganisms involved in methane oxidation in the methane seepage process in the cold seeps in real time, which is helpful to deeply reveal the microscopic mechanism and environmental control factors of the process of methane biochemical conversion in the deep-sea cold seeps, and provides an important means for studying chemosynthesis engineering involving deep-sea methane. In addition, this example provides real-time online monitoring of the process of methane dissolution and phase transformation in the cold seeps, and more accurately checks actual methane content involved in the biochemical conversion process in the cold seeps, providing an important basic means for correct understanding of a methane source and sink mechanism in the ocean.

Compared with closed simulations of the methane seepage process, this example proposes to simulate the methane seepage process in the deep-sea floor in an open system, which is closer to the characteristic that under real conditions, an environmental medium of seepage has material exchange with surrounding fluids in the methane seepage process. Compared with previous studies on the simulation of anaerobic oxidation of methane in the deep sea, this example proposes to monitor the total amount of methane in the reactor and the methane dissolution and phase transformation process in real time and synchronously online, so as to more accurately check the actual methane content involved in the biochemical conversion process in the cold seeps, providing an important basic means for correct understanding of the methane source and sink mechanism in the ocean. Compared with previous studies on anaerobic oxidation of methane in the cold seeps, this example proposes to use a pressure-resistant membrane biological assembly 4 to construct a membrane bioreactor in the high-pressure environment to improve the enrichment efficiency of biomembranes involved in the methane oxidation process, and proposes to invert the thickness changes of the biomembrane on the membrane assembly in the high-pressure environment based on online acoustic monitoring to represent the efficiency of anaerobic oxidation of methane. In addition, through online sampling in a pressure-holding environment, dynamic change characteristics of microorganisms on the membrane assembly are analyzed, providing an advanced means to correct understanding of anaerobic oxidation of methane in the deep sea.

In a specific implementation process, this example further proposes real-time online measurement and analysis on various environmental parameters during methane biochemical conversion, so as to quantitatively understand main control factors of the methane conversion process.

More specifically, the fluid supply unit 102 includes a methane dissolution vessel 1021, an injection pump 1022, a low-temperature water bath vessel 1023, a mechanical stirring device 1024, a back pressure valve 1025, a microflow pump 1026 and a seawater culture medium preparation vessel 1027. The methane dissolution vessel 1021 is disposed in the low-temperature water bath vessel 1023 to ensure that methane-containing fluid is unable to cause heat flow disturbance due to a temperature difference when entering the membrane bioreactor 101 for the deep-sea cold seeps, and the simulation process is not affected. The methane dissolution vessel 1021 is provided with a gas inlet, a liquid inlet and a liquid outlet. The methane dissolution vessel 1021 is connected to the pressurization system 103 through the gas inlet. The methane dissolution vessel 1021 is connected to the seawater culture medium preparation vessel 1027 and the injection pump 1022 in sequence through the liquid inlet. The methane dissolution vessel 1021 is connected to the microflow pump 1026 through the liquid outlet, and the saturated methane fluid is injected into the membrane bioreactor 101 for the deep-sea cold seeps through the microflow pump 1026 at a microflow. A second temperature sensor 10211 and a second pressure sensor 10212 are disposed in the methane dissolution vessel 1021 for monitoring temperature and pressure data in the methane dissolution vessel 1021 and transmitting the data to the control and acquisition terminal 9. The mechanical stirring device 1024 is disposed on a top of the methane dissolution vessel 1021 for enhancing solute dissolution in the methane dissolution vessel 1021. The back pressure valve 1025 is disposed on the top of the methane dissolution vessel 1021 for ensuring that the methane dissolution vessel 1021 completes a dissolution process at set pressure.

In a specific implementation process, the methane dissolution vessel 1021 is disposed in the low-temperature water bath vessel 1023 further for making the system in line with the characteristic of a small temperature difference with an ambient medium when the methane-containing fluid seeps into a seepage area under a seafloor condition closer to the real condition.

More specifically, in a simulation process of the fluid supply unit 102, a temperature of the methane dissolution vessel 1021 is set to be consistent with that of the membrane bioreactor 101 for the deep-sea cold seeps, and is an actual seafloor temperature, but pressure of the methane dissolution vessel needs to be monitored to be lower than phase equilibrium pressure of methane hydrate formation under the temperature condition, so as to avoid formation of methane hydrate in the methane dissolution vessel 1021.

More specifically, the pressurization system 103 includes an air compressor, a booster pump, a gas storage tank, a regulating valve and a pipe valve member. The pressurization system 103 is connected to the gas inlet of the fluid supply unit 102 and a gas inlet of the membrane bioreactor 101 for the deep-sea cold seeps through the pipe valve member. The air compressor is connected to an input end of the gas storage tank through the booster pump. An output end of the gas storage tank is provided with the regulating valve, and connected to the pipe valve member through the regulating valve for injecting gas with specific components into the fluid supply unit 102 and the membrane bioreactor 101 for the deep-sea cold seeps at a set flow.

The above-mentioned solution is implemented with the capacity of simulating the continuous methane seepage process under the deep-sea in-situ temperature and pressure environment conditions. By constructing the membrane biological assembly in the high-pressure environment for membrane forming and growth of the microorganisms in the deep-sea cold seeps, measuring the thickness changes of the biomembrane on the membrane assembly online through ultrasonic monitoring, obtaining the biomembrane samples by pressure holding under the high-pressure condition for sequencing analysis, and combining with other chemical sensor measurement and real-time sampling test analysis, the characteristics of anaerobic oxidation of methane in the cold seeps and the influence of environmental conditions on anaerobic oxidation of methane are quantitatively studied. Compared with existing simulations of methane biochemical conversion processes in deep-sea cold seeps, which ignore the characteristics of methane dissolution and phase transformation in a high-pressure and low-temperature environment, this solution simultaneously monitors the amount of methane dissolution and phase transformation in the reactor during methane seepage, thereby more accurately quantitatively studying the characteristics of anaerobic oxidation of methane in the cold seeps. An important technical tool is provided for accurately understanding the biochemical conversion process and mechanism of methane release from the deep-sea floor.

Example 3

On the basis of Example 2, this example is provided to more clearly illustrate the implementation process of this solution.

As shown in FIG. 2 and FIG. 3, an online environmental parameter measurement system for a membrane bioreaction in deep-sea cold seeps is provided, and a membrane bioreactor 101 for the deep-sea cold seeps is the core of the system. The system mainly includes a fluid supply unit 102, the membrane bioreactor 101 for the deep-sea cold seeps, a pressurization system 103, and a control and acquisition terminal 9. In order to approach the characteristic that under real seafloor conditions, a methane-containing fluid has a small temperature difference from an ambient medium when seeping into a seepage area, a methane dissolution vessel 1021 involved in the system is placed in a low-temperature water bath vessel 1023 to ensure that no large temperature difference occurs when the methane-containing fluid enters the membrane bioreactor 101 for the deep-sea cold seeps, thus avoiding heat flow disturbance. The methane dissolution vessel 1021 is a pressure-resistant vessel, and is provided with a second temperature sensor 10211 and a second pressure sensor 10212. A mechanical stirring device 1024 is disposed on a top of the methane dissolution vessel to enhance solute dissolution in the reactor. A temperature of the 1021 is set to be consistent with that of the membrane bioreactor 101 for the deep-sea cold seeps, and is the same as an actual seafloor temperature. Pressure of the methane dissolution vessel 1021 needs to be monitored to be lower than phase equilibrium pressure of methane hydrate formation under the temperature condition, so as to avoid formation of methane hydrate in the methane dissolution vessel 1021. A back pressure valve 1025 is disposed on the top of the methane dissolution vessel 1021 for ensuring that a dissolution process is performed under a set pressure condition. A microbial culture medium in a seawater culture medium preparation vessel 1027 is injected into the methane dissolution vessel 1021 by an injection pump 1022 through a regulating valve. A saturated methane fluid in the methane dissolution vessel 1021 is injected into the membrane bioreactor 101 for the deep-sea cold seeps by a microflow pump 1026.

The membrane bioreactor 101 for the deep-sea cold seeps mainly includes a sediment simulation chamber 1, a seawater simulation chamber 2, a water bath jacket 10, and other pressure-resistant membrane assemblies. The membrane bioreactor 101 for the deep-sea cold seeps is of a corrosion and pressure resistant structure with a diameter of 200 mm and a height of 250 mm. An inlet of the membrane bioreactor for the deep-sea cold seeps is connected to the microflow pump 1026. The membrane bioreactor 101 for the deep-sea cold seeps mainly includes two parts: the sediment simulation chamber 1 with a height of 100 mm on the lower part and the seawater simulation chamber 2 with a height of 150 mm on the upper part. The two parts are connected through flanges. A resistivity measurement system 6 is disposed in the sediment simulation chamber 1 for monitoring and measuring saturation changes of methane hydrate formation in sediments in a process of methane seepage simulation. Resistivity measurement points are evenly distributed in three layers, with 4×4=16 points distributed in each layer. Temperature sensors 31 are disposed in the sediment simulation chamber 1 and the seawater simulation chamber 2 respectively to monitor changes of environmental temperature in the process of methane seepage simulation. A methane sensor 32 is disposed in the seawater simulation chamber 2 for monitoring changes of methane concentration in the seawater simulation chamber 2. A pressure-resistant membrane biological assembly 4 is disposed in the seawater simulation chamber 2 for monitoring formation of methanotroph and sulfate reducing bacteria biomembranes in a seawater environment. In order to facilitate video observation in the formation process of the biomembranes, front and rear pressure-resistant visible windows 21 are provided in the seawater environment part. In addition, an online pressure-holding biomembrane sampling element 5 is disposed on a top of the membrane bioreactor 101 for the deep-sea cold seeps. As for the element, a sampling ring device is placed in a telescopic pressure-resistant cylinder for scraping biomembrane samples from different positions of the pressure-resistant membrane biological assembly 4 for sequencing analysis in the formation process of the biomembranes. The pressure-resistant membrane biological assembly 4 involved in the system is mainly a porous membrane assembly sintered from seawater corrosion-resistant and pressure-resistant titanium alloy powder, with a height of 120 mm. The pressure-resistant membrane biological assembly is suspended in the seawater environment of the membrane bioreactor 101 for the deep-sea cold seeps. A PID valve 71 is disposed at an outlet of the membrane bioreactor 101 for the deep-sea cold seeps. Pressure stability in the kettle is ensured through regulation of the PID valve 71 in the whole process of methane seepage simulation. The outlet of the membrane bioreactor 101 for the deep-sea cold seeps is connected to a gas-liquid storage tank 72 with a pressure sensor and temperature sensor monitoring function, and the tank is used for collecting and measuring the volume of gas and liquid discharged from the reactor. In the whole process of methane seepage simulation, an inlet and an outlet of the gas-liquid storage tank 72 are opened at the same time to maintain a continuous seepage process, which approaches a situation that under real seafloor environmental conditions, an environmental medium of methane seepage has material exchange with the ambience. In order to facilitate observation through the pressure-resistant visible windows 21, the membrane bioreactor 101 for the deep-sea cold seeps adopts a jacketed water bath for temperature control, that is, the water bath jacket 10 is disposed around the reactor, and is filled with a circulating refrigeration liquid, and an insulation layer is disposed on an outer wall of the water bath jacket 10 to ensure a low-temperature environment of the sediment simulation chamber 1 and the seawater simulation chamber 2. The fluid supply unit 102 and the membrane bioreactor 101 for the deep-sea cold seeps are both connected to the pressurization system 103, and gas may be injected into the pressure-resistant vessels of the two parts for pressurization. The pressurization system 103 involved in the system is mainly composed of fittings such as an air compressor, a booster pump, a gas storage tank, a pressure regulating valve, and a pipe valve member.

As for the main structure of an environmental parameter measurement device involved in the system, the methane sensor 32 is used for monitoring the changes of methane concentration in the reactor; the temperature sensor 31 monitors temperature changes; the pressure sensor 33 monitors pressure changes; an ultrasonic probe 81 and an acoustic wave generator-oscilloscope 82 monitor thickness changes of a biomembrane on the pressure-resistant membrane biological assembly 4; and the resistivity measurement system 6 in a deposited layer monitors the saturation changes of methane hydrate formation in the deposited layer in the methane seepage process.

The control and acquisition terminal 9 involved in this example is used for realizing monitoring of changes of various environmental data information in the process of methane seepage simulation, as well as real-time acquisition, processing, storage, image output and other functions.

A main use method for the system involved in this example mainly includes: first, the membrane bioreactor 101 for the deep-sea cold seeps is assembled from bottom to top, and the sediment simulation chamber 1 is filled with actual deep-sea sediments from Haima cold seeps of South China Sea in sequence. The seawater simulation chamber 2 is then filled with actual deep-sea seawater sampled from the Haima cold seeps. Then the water bath jacket 10 is started to keep the temperature in the reactor consistent with temperature conditions at deep-sea floor in the seepage process. Then the pressurization system 103 is started, and nitrogen gas is injected into the membrane bioreactor 101 for the deep-sea cold seeps for simulating the seepage process, such that a pressure value in the reactor is increased to 14 MPa. Then a prepared nutrient solution is injected into the seawater culture medium preparation vessel 1027, dissolved gas in the methane dissolution vessel 1021 is injected into the membrane bioreactor 101 for the deep-sea cold seeps, and the pressure in the methane dissolution vessel 1021 does not exceed 2 MPa through constant-pressure control. The low-temperature water bath vessel 1023 of the methane dissolution vessel 1021 is opened to enable the temperature in the methane dissolution vessel 1021 and the temperature in the membrane bioreactor 101 for the deep-sea cold seeps to be 4° C. Then the mechanical stirring device 1024 is started, an outlet of the methane dissolution vessel 1021, the microflow pump 1026, and the inlet and outlet of the membrane bioreactor 101 for the deep-sea cold seeps are opened in sequence when methane in the methane dissolution vessel 1021 reaches saturation, and a saturated methane solution is continuously injected into the membrane bioreactor 101 for the deep-sea cold seeps at a rate of 10 ml/min. In the whole simulation process, the pressure condition in the kettle for simulating the seepage process is kept constant at 14 MPa through constant-pressure control, and is consistent with actual environmental conditions in the deep sea. In the whole process, during the seepage process a liquid inlet channel and the outlet of the membrane bioreactor 101 for the deep-sea cold seeps are both in an open state, so as to simulate the methane seepage process having material exchange with ambient conditions. In the process of methane seepage simulation, the changes of parameters such as temperature, pressure, resistivity, acoustic wave, and methane concentration in the membrane bioreactor 101 for the deep-sea cold seeps are monitored in real time, sampling is carried out from different positions of seawater and the deposited layer through double valve piston samplers 11, and chemical components and concentration changes of samples, as well as the thickness of a biomembrane and microbial group changes are analyzed. As a result, biomembrane growth characteristics and environmental parameter regulation characteristics of the membrane bioreactor in the methane seepage process can be monitored in real time.

It is apparent that the above examples of the present invention are merely examples of the present invention for purposes of clarity and are not intended to limit the implementations of the present invention. For those of ordinary skill in the art, various other modifications or variations can be made on the basis of the above description. All implementations need not to be, and cannot be, exhaustive. Any modifications, equivalent replacements and improvements made within the spirit and principle of the present invention shall fall within the protection scope of the claims of the present invention.

What is claimed is:

1. A membrane bioreactor for deep-sea cold seeps, comprising a control and acquisition terminal, the membrane bioreactor for deep-sea cold seeps further comprises a sediment simulation chamber, a seawater simulation chamber, a sensor group, a pressure-resistant membrane biological assembly, an online pressure-holding biomembrane sampling element, a resistivity measurement system, a pressure regulation assembly and an ultrasonic observation assembly, wherein the sediment simulation chamber is disposed below the seawater simulation chamber, and is in flanged connection to the seawater simulation chamber; the sensor group is disposed in the sediment simulation chamber and the seawater simulation chamber, and a signal output end of the sensor group is electrically connected to the control and acquisition terminal;

the pressure-resistant membrane biological assembly is disposed in the seawater simulation chamber for monitoring formation of a colony biomembrane in a seawater environment;

the online pressure-holding biomembrane sampling element is disposed on a top of the seawater simulation chamber, and a control end of the online pressure-holding biomembrane sampling element is electrically connected to the control and acquisition terminal for scraping biomembrane samples from different positions of the pressure-resistant membrane biological assembly for sequencing and analysis in a formation process of the biomembrane;

the resistivity measurement system is disposed in the sediment simulation chamber, and a signal output end of the resistivity measurement system is electrically connected to the control and acquisition terminal for monitoring and measuring saturation changes of methane hydrate formation in sediments in a process of methane seepage simulation;

the pressure regulation assembly is connected to the seawater simulation chamber through a pipeline, and a control end of the pressure regulation assembly is electrically connected to the control and acquisition terminal for regulating and controlling pressure in the reactor to ensure pressure stability in the reactor; and an ultrasonic probe of the ultrasonic observation assembly is disposed in the seawater simulation chamber for monitoring thickness changes of the biomembrane on the pressure-resistant membrane biological assembly and outputting a signal to the control and acquisition terminal;

the pressure-resistant membrane biological assembly is a porous membrane assembly sintered from seawater corrosion-resistant and pressure-resistant titanium alloy powder, and is suspended in the seawater simulation chamber;

the online pressure-holding biomembrane sampling element comprises a telescopic pressure-resistant cylinder, a sampling ring device and a pressure-holding device, wherein the telescopic pressure-resistant cylinder is disposed on the top of the seawater simulation chamber, the sampling ring device is placed in the telescopic pressure-resistant cylinder, and the pressure-holding device is fixedly connected outside the telescopic pressure-resistant cylinder in a sleeving manner; and a control end of the sampling ring device and a control end of the pressure-holding device are both electrically connected to the control and acquisition terminal.

2. The membrane bioreactor for deep-sea cold seeps according to claim 1, wherein the sensor group comprises temperature sensors, a methane sensor and a pressure sensor, wherein the temperature sensors are disposed in the sediment simulation chamber and the seawater simulation chamber for monitoring changes of an environmental temperature in the sediment simulation chamber and the seawater simulation chamber, and signal output ends of the temperature sensors are electrically connected to the control and acquisition terminal;

the methane sensor is disposed in the seawater simulation chamber for monitoring changes of methane concentration in the seawater simulation chamber, and a signal output end of the methane sensor is electrically connected to the control and acquisition terminal; and the pressure sensor is disposed in the seawater simulation chamber for monitoring changes of pressure in the reactor, and a signal output end of the pressure sensor is electrically connected to the control and acquisition terminal.

3. The membrane bioreactor for deep-sea cold seeps according to claim 1, wherein the pressure regulation assembly comprises a PID valve and a gas-liquid storage tank; the gas-liquid storage tank is connected to the seawater simulation chamber through a pipeline; and the PID valve is disposed on the pipeline and electrically connected to the control and acquisition terminal.

4. The membrane bioreactor for deep-sea cold seeps according to claim 1, wherein the ultrasonic observation assembly further comprises an acoustic wave generator-oscilloscope; and a signal output end of the ultrasonic probe is electrically connected to a signal input end of the acoustic wave generator-oscilloscope and the control and acquisition terminal.

5. The membrane bioreactor for deep-sea cold seeps according to claim 1, wherein the membrane bioreactor for deep-sea cold seeps further comprises pressure-resistant visible windows provided in the seawater simulation chamber.

6. The membrane bioreactor for deep-sea cold seeps according to claim 5, wherein the membrane bioreactor for deep-sea cold seeps further comprises double valve piston samplers disposed in the sediment simulation chamber and the seawater simulation chamber.

7. The membrane bioreactor for deep-sea cold seeps according to claim 5, wherein the membrane bioreactor for deep-sea cold seeps further comprises a water bath jacket disposed around the reactor, and a control end of the water bath jacket is electrically connected to the control and acquisition terminal.

8. An online environmental parameter measurement system for a membrane biological reaction in deep-sea cold seeps, the online environmental parameter measurement system comprises the membrane bioreactor for the deep-sea cold seeps according to claim 1, a fluid supply unit and a pressurization system, wherein the fluid supply unit is configured to generate saturated methane fluid and inject the saturated methane fluid into the membrane bioreactor for the deep-sea cold seeps at a microflow;

the membrane bioreactor for the deep-sea cold seeps simulates a biomembrane growth process during anaerobic oxidation of methane (AOM) in the cold seeps and monitors changes of environmental conditions of anaerobic oxidation of methane;

the membrane bioreactor for the deep-sea cold seeps and the fluid supply unit are both connected to the pressurization system to ensure stability and consistency of internal environmental pressure of the system in a simulation process; and the fluid supply unit and the pressurization system are both electrically connected to a control and acquisition terminal to realize information interaction.

9. The online environmental parameter measurement system for a membrane biological reaction in deep-sea cold seeps according to claim 8, wherein the fluid supply unit comprises a methane dissolution vessel, an injection pump, a low-temperature water bath vessel, a mechanical stirring device, a back pressure valve, a microflow pump and a seawater culture medium preparation vessel, wherein the methane dissolution vessel is disposed in the low-temperature water bath vessel to ensure that methane-containing fluid is unable to cause heat flow disturbance due to a temperature difference when entering the membrane bioreactor for the deep-sea cold seeps, and the simulation process is not affected; the methane dissolution vessel is provided with a gas inlet, a liquid inlet and a liquid outlet; the methane dissolution vessel is connected to the pressurization system through the gas inlet; the methane dissolution vessel is connected to the seawater culture medium preparation vessel and the injection pump in sequence through the liquid inlet; the methane dissolution vessel is connected to the microflow pump through the liquid outlet, and the saturated methane fluid is injected into the membrane bioreactor for the deep-sea cold seeps through the microflow pump at a microflow;

a second temperature sensor and a second pressure sensor are disposed in the methane dissolution vessel for monitoring temperature and pressure data in the methane dissolution vessel and transmitting the data to the control and acquisition terminal;

the mechanical stirring device is disposed on a top of the methane dissolution vessel for enhancing solute dissolution in the methane dissolution vessel; and the back pressure valve is disposed on the top of the methane dissolution vessel for ensuring that the methane dissolution vessel completes a dissolution process at set pressure.

10. The online environmental parameter measurement system for a membrane biological reaction in deep-sea cold seeps according to claim 9, wherein in a simulation process of the fluid supply unit, a temperature of the methane dissolution vessel is set to be consistent with that of the membrane bioreactor for the deep-sea cold seeps, and is an actual seafloor temperature, but pressure of the methane dissolution vessel is lower than phase equilibrium pressure of methane hydrate formation under the temperature condition, so as to avoid formation of methane hydrate in the methane dissolution vessel.

11. The online environmental parameter measurement system for a membrane biological reaction in deep-sea cold seeps according to claim 10, wherein the pressurization system comprises an air compressor, a booster pump, a gas storage tank, a regulating valve and a pipe valve member, wherein the pipe valve member is connected to the gas inlet of the fluid supply unit and a gas inlet of the membrane bioreactor for the deep-sea cold seeps through the pipe valve member; the air compressor is connected to an input end of the gas storage tank through the booster pump; and an output end of the gas storage tank is provided with the regulating valve, and the regulating valve is connected to the pipe valve member for injecting specific gas into the fluid supply unit and the membrane bioreactor for the deep-sea cold seeps.

12. The online environmental parameter measurement system for a membrane biological reaction in deep-sea cold seeps according to claim 9, wherein the pressurization system comprises an air compressor, a booster pump, a gas storage tank, a regulating valve and a pipe valve member, wherein the pipe valve member is connected to the gas inlet of the fluid supply unit and a gas inlet of the membrane bioreactor for the deep-sea cold seeps through the pipe valve member; the air compressor is connected to an input end of the gas storage tank through the booster pump; and an output end of the gas storage tank is provided with the regulating valve, and the regulating valve is connected to the pipe valve member for injecting specific gas into the fluid supply unit and the membrane bioreactor for the deep-sea cold seeps.

* * * * *